United States Patent
Powell et al.

Patent Number: 5,515,869
Date of Patent: May 14, 1996

[54] PEDIATRIC SPINAL IMMOBILIZATION AND AIRWAY CONTROL BOARD

[76] Inventors: Joseph S. Powell; Kelly A. Buckley, both of P.O. Box 535, Big Bear City, Calif. 92314

[21] Appl. No.: 412,217

[22] Filed: Mar. 27, 1995

Related U.S. Application Data

[63] Continuation of Ser. No. 269,432, Jun. 30, 1994, abandoned.
[51] Int. Cl.$^6$ ............................. A61F 5/37; A47B 1/00
[52] U.S. Cl. ........................ 128/870; 128/876; 5/628
[58] Field of Search ........................... 128/845, 846, 128/869–876; 5/625, 628, 636, 637

[56] References Cited

U.S. PATENT DOCUMENTS

| | | | |
|---|---|---|---|
| 3,933,154 | 1/1976 | Cabansag | 128/870 |
| 4,151,842 | 5/1979 | Miller | 5/628 |
| 4,612,678 | 9/1986 | Fitsch | 128/870 |
| 4,655,206 | 4/1987 | Moody | 128/870 |
| 4,757,811 | 7/1988 | Clark | 269/328 |
| 4,979,520 | 12/1990 | Boone | 128/876 |
| 5,048,136 | 9/1991 | Popitz | 5/636 |
| 5,334,133 | 8/1994 | Carroll | 128/870 |

*Primary Examiner*—Michael A. Brown

[57] ABSTRACT

A pediatric spinal immobilization board for properly immobilizing a pediatric trauma patient prior, and during transportation to an appropriate medical facility. The board includes two rigid panels 10 and 18 which support the weight of the patient's body and head. The panel at the patient's head 18 is located inferior to the panel 10 that supports the patient's body. This dual planed system allows for neutral alignment of the patient's cervical spine and an open pediatric airway. The board is affixed with a plurality of flexible, adjustable, and easily removable restraining straps. These straps are used to effectively restrain the patient to the rigid planes. The straps attach to the board, to each other, and to themselves via a hook-and-latch or other easily connective and removable fastening system. The board is afforded multiple slots that receive the hands of the rescuers to aid in ease of patient transportation to and from a transportation vehicle.

7 Claims, 2 Drawing Sheets

PEDIATRIC SPINAL IMMOBILIZATION AND AIRWAY CONTROL BOARD

This is a continuation of application Ser. No. 06/3,094 now abandoned.

BACKGROUND

1. Field of the Invention

This invention relates to a splinting device, specifically to an improved rigid splinting device for proper spinal immobilization and airway control of the pediatric trauma patient.

2. Discussion of Prior Art

It has become common knowledge in the field of emergency medicine, that extreme caution and care is necessary in the movement and/or transportation of the trauma victim. Any improper movement can result in further injury to the patient. Many times in the event of a cervical spinal injury, the cervical vertebra is severely fractured while the internal spinal cord remains intact. Improper movement will often result in injury to, and/or a complete detachment of, the previously uninjured spinal cord. Specific injuries caused by improper movement range from minor pain to permanent paralysis and irreversible death.

It has become specifically determined that the pediatric trauma patient has a propensity for spinal cord injuries resulting from trauma. This is due to the fact that, compared to adults, pediatric patients have a large head mass (weight and size) in proportionate to their bodies. Pediatric patients also have very weak and poorly developed neck and shoulder muscles to support this increased mass. Therefore, it is of paramount importance to keep the pediatric trauma patient immobile and their spinal column in neutral alignment during all handling, packaging, and transportation to an appropriate medical facility.

Numerous devices have been developed for immobilizing the adult trauma victim, but very few are made specifically for the pediatric patient.

The following are the most pertinent adult spinal immobilization devices patents known to the applicants. This art clearly illustrates the novelty of the applicant's invention.

| | | | |
|---|---|---|---|
| 2,247,360 | 3,158,875 | 3,707,734 | 3,151,343 |
| 2,361,328 | 3,315,671 | 3,732,863 | 3,566,422 |
| 2,361,789 | 3,449,776 | 3,737,923 | |
| 2,409,934 | 3,469,268 | 3,797,051 | |
| 2,511,061 | 3,526,222 | 3,889,668 | |

There are no pertinent patents related to pediatric spinal immobilization known to the applicants.

Current state of the art in pediatric spinal immobilization relates to a flat, single plane rigid board much like many the above noted patents. The exception being a smaller version to accommodate the smaller pediatric patient. Current state of the art also has a plurality of fixed straps to immobilize and restrain the patient to the splinting device.

The pediatric patient is different from the adult in that the pediatric patient's head is disproportionatly large. When you place the pediatric patient on a flat, single plane surface, it causes the patient's cervical spine and head to flex forward (anteriorly).

A. The above noted flexion causes undo movement of the pediatric cervical spine. This unnecessary movement can cause permanent paralysis or death as the fractured cervical spine severs the spinal cord.

B. Flexion of the neck also causes closure of the pediatric trauma patients airway. This closure creates an airway obstruction and prohibits oxygen from entering the body. The results are permanent brain damage and/or death from hypoxic (lack of oxygen) brain injury.

C. The current state of the art also provides a plurality of fixed straps to restrain the patient to the splinting device. These fixed straps do not allow adjustment for varying ages of pediatric patients. This often results in poor immobilization and further injury to the patient's cervical spine.

D. Fixed straps do not adjust; therefore, they do not allow for immobilization of the lower leg of a patient with an intraosseous infusion needle in place. An intraosseous infusion needle is a device placed in the lower leg bone to provide needed emergency medications and fluids to the patient. The lower leg of a patient with a intraosseous infusion needle in place must be immobilized. If the patient's leg is not properly immobilized, the needle can become dislodged and will be ineffective. Proper immobilization can be impossible to accomplish with fixed straps.

E. Much of the current state of the art utilizes very porous materials in the construction of their splinting devices. This is a problem, as frequently these devices become soaked with infectious bodily fluids. Once soaked, these porous materials are extremely difficulty to properly clean and/or disinfect. This greatly increases the risk of transmission of infectious and deadly diseases to future patients and rescuers.

F. The current state of the art uses fixed or very difficult to remove restraining straps. Once again, this is a problem as these straps frequently become saturated with infectious bodily fluids. This feature makes it difficult to properly clean and/or disinfect these straps. As noted above, this increases the risk of infectious and deadly diseases being transmitted to patients and the rescue team.

OBJECT AND ADVANTAGES

Accordingly, several objects and advantages of applicant's invention are as follows. These objects and advantages also show the novelty of the applicant's invention over prior art and current state of the art.

The improved splint is a dual plane, spinal immobilization device. There is a main plane being of flat, rigid design. The patient's body is fully immobilized utilizing a plurality of flexible adjustable restraining straps. These straps hold the patient's body securely and without undo movement to the surface of the main plane. There is a secondary plane located ¾ of an inch inferior (below) and parallel to the main plane of the device inferior being defined as situated under or beneath; lower. The secondary plane is of flat, rigid design. The secondary plane has flexible adjustable restraining straps along with two suitable padded head restraining devices. These fully immobilize the patient's head to the surface of the secondary plane.

A. The dual planed system allows for the traumatic large head of the pediatric patient to rest on the surface of the secondary plane. The head is then situated ¾ of an inch below (inferior to) the main plane surface where the body of the patient rests. This allows for proper neutral alignment of the patient's cervical spine and greatly reduces the unnecessary movement and improper alignment of the patient's injured cervical spine. The end result of the improved device is a significant decrease in the unnecessary and easily rectifiable number of cervical spinal cord lesions. These lesions result in permanent paralysis and irreversible death to the young patient.

B. The dual plane system also eliminates the anterior flexion (chin to chest) of the immobilized trauma patient's head. This allows for a fully open, clear, and unobstructed pediatric airway in the fully immobilized trauma patient. The results are proper air exchange and proper oxygen delivery to the tissues and organs of the body. Once again, this improved device results in the reduction of unnecessary brain damage and irreversible death caused by single planed spinal immobilization systems.

C. The improved device is affixed with a plurality of flexible adjustable restraining straps. This allows for proper immobilization of varying sizes of pediatric patients, unlike current state of the art.

D. These adjustable straps allow for proper placement around the intraosseous infusion needle. This creates a fully immobilized lower leg. The results being a significant decrease in needle dislodgement from patient movement.

E. The main and secondary planes of this improved splinting device are constructed of a smooth, non-porous material. The non-porous material resists the absorption of infectious bodily fluids and increase the ease of washing ability. This greatly decreases the risk of infection to future patients and the rescue team.

F. All adjustable restraining straps are affixed to the main and secondary planes, via a hook-and-latch system. Other rapidly and easily removable connecting mechanisms can be used. This allows for proper washing and disinfecting, and once again reduces the risk of transmitting infectious diseases to patients and rescuers.

Further objects and advantages of the applicant's invention will become apparent from consideration of the drawings and description contained herein.

REFERENCE NUMERALS IN DRAWINGS

10 Main Rigid Panel or Plane
12 Hand Receptacle
14 Hand Receptacle
16 Hand Receptacle
18 Secondary Rigid Panel or Plane
20 Forehead restraining Strap
22 Chin Restraining Strap
24 Soft Immobilization Block
26 Soft Immobilization Block
28 Shoulder and Chest Restraining Strap
30 Shoulder and Chest Restraining Strap
32 Attachment Point
34 Attachment Point
36 Shoulder Strap Fastening Pin
38 Shoulder Strap Fastening Pin
40 Main and Secondary Plane Attachment Point and Drop Area
42 Adjustable Chest Restraining Strap
44 Attachment Point
46 Adjustable Chest Restraining Strap
48 Attachment Point
50 Attachment Point
52 Attachment Point
54 Adjustable abdominal and Pelvic Restraining Strap
56 Attachment Point
58 Restraining Strap Adjustment and Anchoring Slot
60 Attachment Point
62 Adjustable Abdominal and Pelvic Restraining Strap
64 Attachment Point
66 Restraining Strap Adjustment and Anchoring Slot
68 Restraining Strap Adjustment and Anchoring Slot
70 Attachment Point
72 Adjustable Leg Restraining Strap
74 Attachment Point
76 Adjustable Leg Restraining Strap
78 Attachment Point
80 Attachment Point
82 Restraining Strap Adjustment and Anchoring Slot
84 Attachment Point
86 Adjustable Leg Restraining Strap
88 Attachment Point
90 Adjustable Leg Restraining Strap
92 Attachment Point
94 Attachment Point
96 Attachment Point
98 Attachment Point
100 Slot for Shoulder Strap
102 Slot for Shoulder Strap
104 Attachment Point
106 Cervical Spine
108 Pediatric Airway

DESCRIPTION—FIGS. 1 to 4

Figure 1:
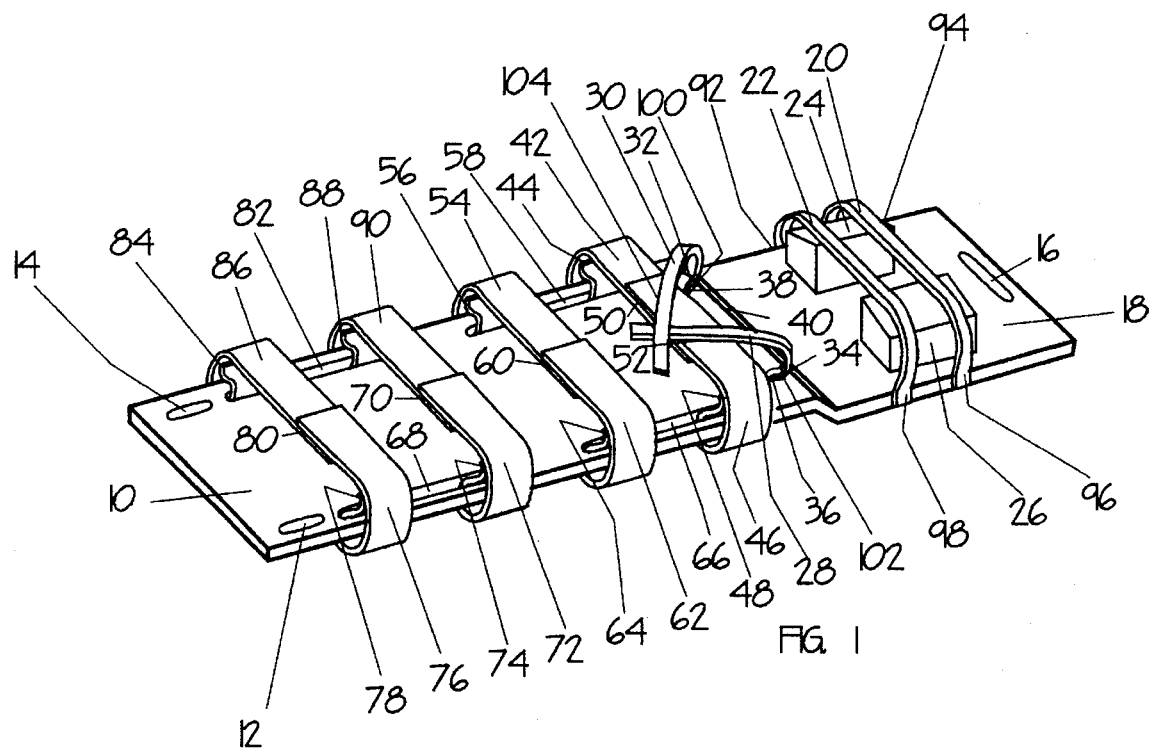
FIG. 1 is a perspective view of one embodiment of the improved pediatric spinal immobilization and airway control board.

In FIG. 1, a perspective view is shown of the pediatric spinal immobilization and airway control board.

A flat, rigid panel 10 serves as the major supporting device for patient's body. Panel 10 is also referred to in this application as the main plane. A smaller flat, rigid panel 18 serves as the major supporting device for a patient's head. Panel 18 is also referred to in this application as the secondary plane. Both panel 10 and panel 18 may be constructed from several suitable, non-porous materials such as coated wood, plastic, fiberglass, composites, or other cellular type materials. Ease of manufacture, strength of material, expense, and washing ability are the primary factors for material selection. This application shall not be limited by material selection. Panel 18 is located ¾" inferior (below) to panel 10 creating an appropriate vertical spacing 40 between these two panels. Spacing 40 is accomplished over a 45 degree angle. Panels 10 and 18 are connected at 40.

Slots 12, 14, and 16 serve as hand receptacles for the hands of the rescuers. Slots 82, 68, 66, and 58 serve to create adjustable anchoring points for straps 86, 76, 90, 72, 62, 54, 46, and 42.

A plurality of flexible, adjustable restraining straps are used to secure different portions of the pediatric trauma patient's body to panels 10 and 18 for safe transport to an appropriate medical facility.

Strap 86 feeds through slot 82, wraps around the edge of panel 10 and reattaches to itself at 84 via hook-and-latch or other appropriate fastening system. Strap 76 feeds through slot 68, wraps around the edge of panel 10, and reattaches to itself at 78 via a hook-and-latch or other appropriate fastening system. Straps 86 and 76 fold over the patient's legs and attach to each other at 80 via hook-and-latch or other appropriate fastening system. Straps 86 and 76 combine to properly restrain the lower portion of the patient's legs.

Strap 90 feeds through slot 82, wraps around the edge of panel 10 and reattaches itself at 88 via a hook-and-latch or other appropriate fastening system. Strap 72 feeds through slot 68, wraps around the edge of panel 10, and reattaches itself at 74 via a hook-and-latch or other appropriate fastening system. Straps 88 and 72 fold over the patient's legs and attach to each other at 70 via a hook-and-latch or other appropriate fastening system. Straps 88 and 72 combine to properly restrain the upper portion of the patient's leg.

Strap 54 feeds through slot 58, wraps around the edge of panel 10, and reattaches itself at 56 via a hook-and-latch or other appropriate fastening system. Strap 62 feeds through slot 66, wraps around the edge of panel 10, and reattaches itself at 64 via a hook-and-latch or other appropriate fastening system. Straps 54 and 62 fold over patient's abdominal and pelvic regions and attach at 60 via a hook-and-latch or other appropriate fastening system. Straps 54 and 62 combine to properly restrain the patient's abdominal and pelvic regions.

Straps 42 feeds through slot 58, wraps around the edge of panel 10, and reattaches to itself at 44 via a hook-and-latch or other appropriate fastening system. Strap 46 feeds through slot 66, wraps around the edge of panel 10, and reattaches to itself at 48 via a hook-and-latch or other appropriate fastening system. Straps 42 and 46 fold over the patient's chest and attach to each other at 50 via a hook-and-latch or other appropriate fastening system. Straps 42 and 46 combine to properly restrain the patient's chest region.

Strap 30 feeds through slot 100, wraps around fastening pin 38, and reattaches to itself at 32 via a hook-and-latch or other appropriate fastening system. Strap 30 folds over the patient's right shoulder and attaches to strap 42 at point 104 via hook-and-latch or other appropriate fastening system. Strap 30 serves to properly restrain the patient's right shoulder and upper torso.

Strap 28 feeds through slot 102, wraps around fastening pin 36, and reattaches at 34 via hook-and-latch or other appropriate fastening system. Strap 28 folds over the patient's left shoulder and attaches to strap 46 at point 52 via hook-and-latch or other appropriate fastening system. Strap 28 serves to restrain the patient's left shoulder and upper torso.

Strap 22 folds over restraining block 24, the patient's chin area, and restraining block 26. Strap 22 attaches to the bottom of panel 18 at points 92 and 98 via a hook-and-latch or other appropriate fastening system. Strap 22 runs completely across panel 18. Strap 22 serves to properly restrain the patient's lower head.

Strap 20 folds over restraining block 24, the patient's forehead area, and restraining block 26. Strap 20 attaches to panel 18 at points 94 and 96 via hook-and-latch or other appropriate fastening system. Strap 20 runs completely across panel 18. Strap 20 serves to properly restrain the patient's upper head.

Figure 2:
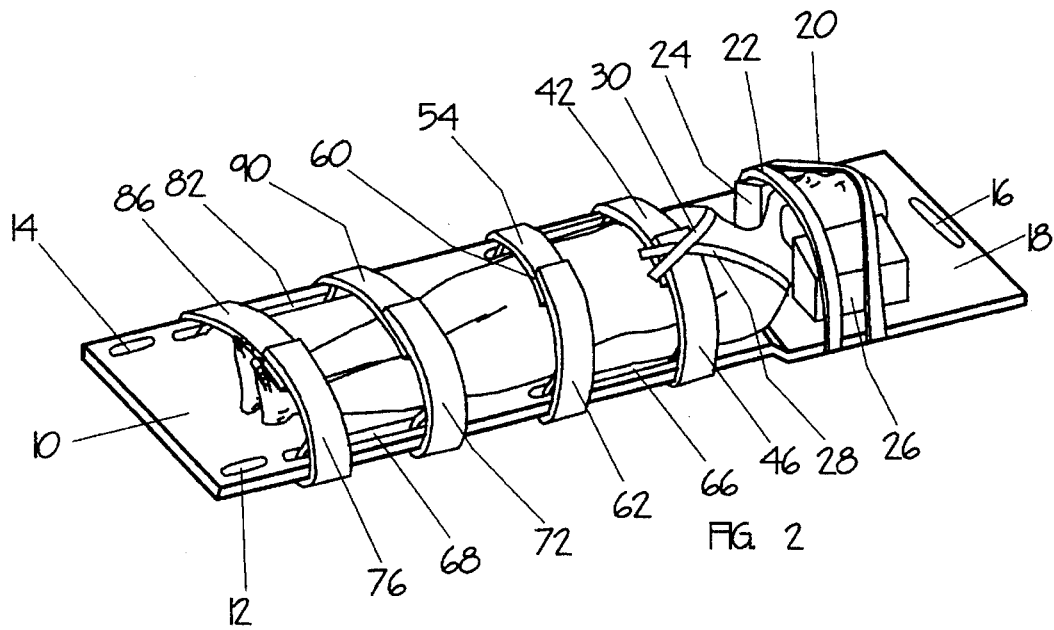
FIG. 2 is a perspective view of said splint showing a properly immobilized pediatric trauma patient in the fully restrained position.

In FIG. 2, there is shown a perspective view of the improved splinting device. FIG. 2 demonstrates the utility of the invention with a trauma patient properly secured onto the device in the fully restrained position. In FIG. 2, straps 86, 76, 90, 72, 54, 62, 42, 46, 30, 28, 22, and 20 along with restraining blocks 24 and 26 serve to fully and properly restrain the pediatric patient to panels 10 and 18.

Figure 3:
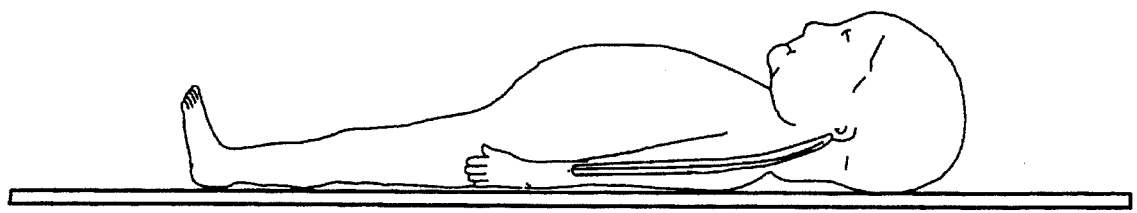
FIG. 3 is a side view of an ineffective single plane, flat, pediatric spinal immobilization splint with an immobilized patient in the fully restrained position.

FIG. 3 is offered to demonstrate the danger and ineffectiveness of prior art and current state of the art. In FIG. 3, the patient's cervical spine is shown in the dangerous and ineffective flexed position. This flexion also causes closure of the pediatric airway. Flexion of spine and closure of airway can once again cause permanent paralysis and irreversible death.

Figure 4:
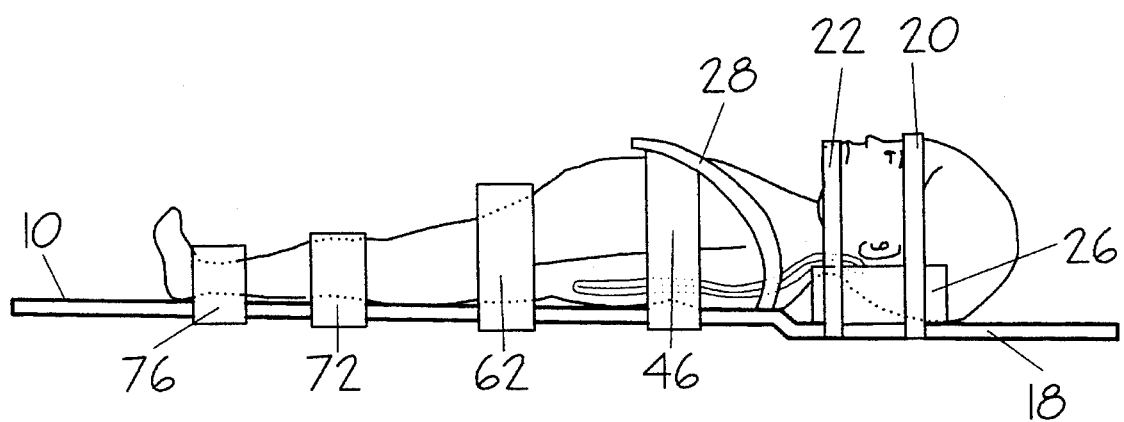
FIG. 4 is a side view of the improved dual plane, spinal immobilization device showing a properly immobilized pediatric patient in the fully restrained position.

FIG. 4 is offered to demonstrate the effectiveness, safety, and novelty of applicants' improved device. In FIG. 4, the patient's cervical spine is in the proper neutral position and the patient's airway is fully open and unobstructed. This once again, allows for safe and effective transportation of the properly restrained patient to an appropriate medical facility.

SUMMARY, RAMIFICATIONS, AND SCOPE

Thus, the reader can see that the pediatric spinal immobilization and airway control board is easily adjustable, simple to apply, affords an ease of washing ability, allows for proper neutral alignment of the pediatric cervical spine, and creates a fully open and unobstructed pediatric airway in the fully immobilized trauma patient.

Although the description above contains many specifications, these should not be considered as limiting the scope of the invention, but as merely providing illustrations of some of the presently preferred embodiments of this invention. For example, the flexible restraining straps can be made of different sizes, shapes, and materials. The head restraining blocks and straps can also be made of different sizes, shapes, and materials such as plastics; disposable foam, cloth, or cardboard; as well as other easily sanitized items.

Accordingly, the scope of this invention should be determined not by the embodiments illustrated, but by the appended claims and their legal equivalents.

What we claim as new is:

1. A full body spinal immobilization splint for use in immobilizing a traumatic pediatric patient throughout the course of medical treatment an improvement comprising of:

a. a rigid main plane of sufficient size to accommodate the body/torso of said traumatic pediatric patient b. a rigid secondary plane of sufficient size as to accommodate the head of said traumatic pediatric patient c. an offset connection means connecting said main plane to said secondary plane d. a means for immobilizing said traumatic pediatric patient's body/torso to said main plane e. a means for immobilizing said traumatic pediatric patient's head to said secondary plane f. whereby said traumatic pediatric patient's head is immobilized inferior to said pediatric patient's body creating a neutral cervical alignment and an open airway in the fully immobilized traumatic pediatric patient.

g. said rigid main plane extends from said offset connection means to one end of the immobilization splint and said rigid secondary plane extends from said offset connection means to another end of the immobilization splint.

2. The splint of claim 1 wherein the main and secondary planes having a means of construction that is non porous as to prevent the absorption of infectious body fluids into the primary and secondary planes
- a. whereby increasing ease of washing ability and decreasing the risk of transmission of infectious diseases to a future patient and the rescue team.

3. The splint described in claim 1 wherein said main plane having elongated slots located at the proximal edges of said main plane to serve as an adjustable anchoring point for said means of immobilizing said pediatric patient's body/torso.

4. The splint described in claim 1 wherein the means of immobilizing the patient's body/torso and head comprise a plurality of flexible adjustable and easily removable restraining straps.

5. The flexible restraining straps of claim 4 wherein connect to the primary and secondary planes via a hook-and-latch connecting system as to allow for rapid removal and ease of washing ability
- a. whereby encouraging rescue workers to properly cleanse the flexible restraining straps, thus decreasing the risk of transmission of infectious diseases to the patient and the rescue team.

6. The flexible restraining straps of claim 4 wherein the flexible straps connect to said elongated slots in said main plane
- a. whereby creating an adjustable anchor for the flexible restraining straps thus allowing for proper immobilization of varying sizes of said pediatric patients.

7. The flexible restraining straps of claim 4 wherein the flexible restraining straps connect to the underside of said secondary plane.

* * * * *